(12) United States Patent
McClymont et al.

(10) Patent No.: US 11,020,102 B2
(45) Date of Patent: Jun. 1, 2021

(54) SWIVEL RETRACTOR AND RIGID CONNECTION SYSTEM FOR RETRACTORS

(71) Applicant: K2M, Inc., Leesburg, VA (US)

(72) Inventors: Kaitlin Elizabeth Ann McClymont, Vienna, VA (US); Josh Rubin, Falls Church, VA (US)

(73) Assignee: K2M, Inc., Leesburg, VA (US)

(*) Notice: Subject to any disclaimer, the term of this patent is extended or adjusted under 35 U.S.C. 154(b) by 126 days.

(21) Appl. No.: 16/030,037

(22) Filed: Jul. 9, 2018

(65) Prior Publication Data

US 2019/0008498 A1 Jan. 10, 2019

Related U.S. Application Data

(60) Provisional application No. 62/530,363, filed on Jul. 10, 2017.

(51) Int. Cl.

| *A61B 17/56* | (2006.01) |
| *A61B 17/60* | (2006.01) |
| *A61F 2/00* | (2006.01) |
| *A61B 17/02* | (2006.01) |
| *A61B 17/70* | (2006.01) |
| *A61B 90/92* | (2016.01) |

(52) U.S. Cl.
CPC .............. *A61B 17/025* (2013.01); *A61B 17/02* (2013.01); *A61B 17/7077* (2013.01); *A61B 90/92* (2016.02); *A61B 17/0206* (2013.01); *A61B 2017/0256* (2013.01)

(58) Field of Classification Search
CPC combination set(s) only.
See application file for complete search history.

(56) References Cited

U.S. PATENT DOCUMENTS

| 5,928,139 | A | 7/1999 | Koros et al. |
| 8,979,749 | B2 | 3/2015 | Gorek et al. |
| 2009/0105769 | A1 | 4/2009 | Rock et al. |
| 2011/0034779 | A1 | 2/2011 | Louftus et al. |
| 2015/0164569 | A1 | 6/2015 | Reitblat et al. |
| 2016/0074029 | A1* | 3/2016 | O'Connell ........... A61B 17/025 600/213 |
| 2016/0345952 | A1 | 12/2016 | Kucharzyk et al. |

* cited by examiner

*Primary Examiner* — Sameh R Boles
(74) *Attorney, Agent, or Firm* — Lerner, David, Littenberg, Krumholz & Mentlik, LLP

(57) ABSTRACT

A swivel distractor includes a blade portion, a flange, and a distraction portion. The flange extends at an angle from a first end of the blade portion. The distraction portion is pivotally coupled to a second end of the blade portion opposite the first end. The distraction portion may include a first foot that is configured to be received in a head of a first pedicle screw and a second foot that is configured to be received in a head of a second pedicle screw. The second foot may be movable relative to the first foot.

20 Claims, 17 Drawing Sheets

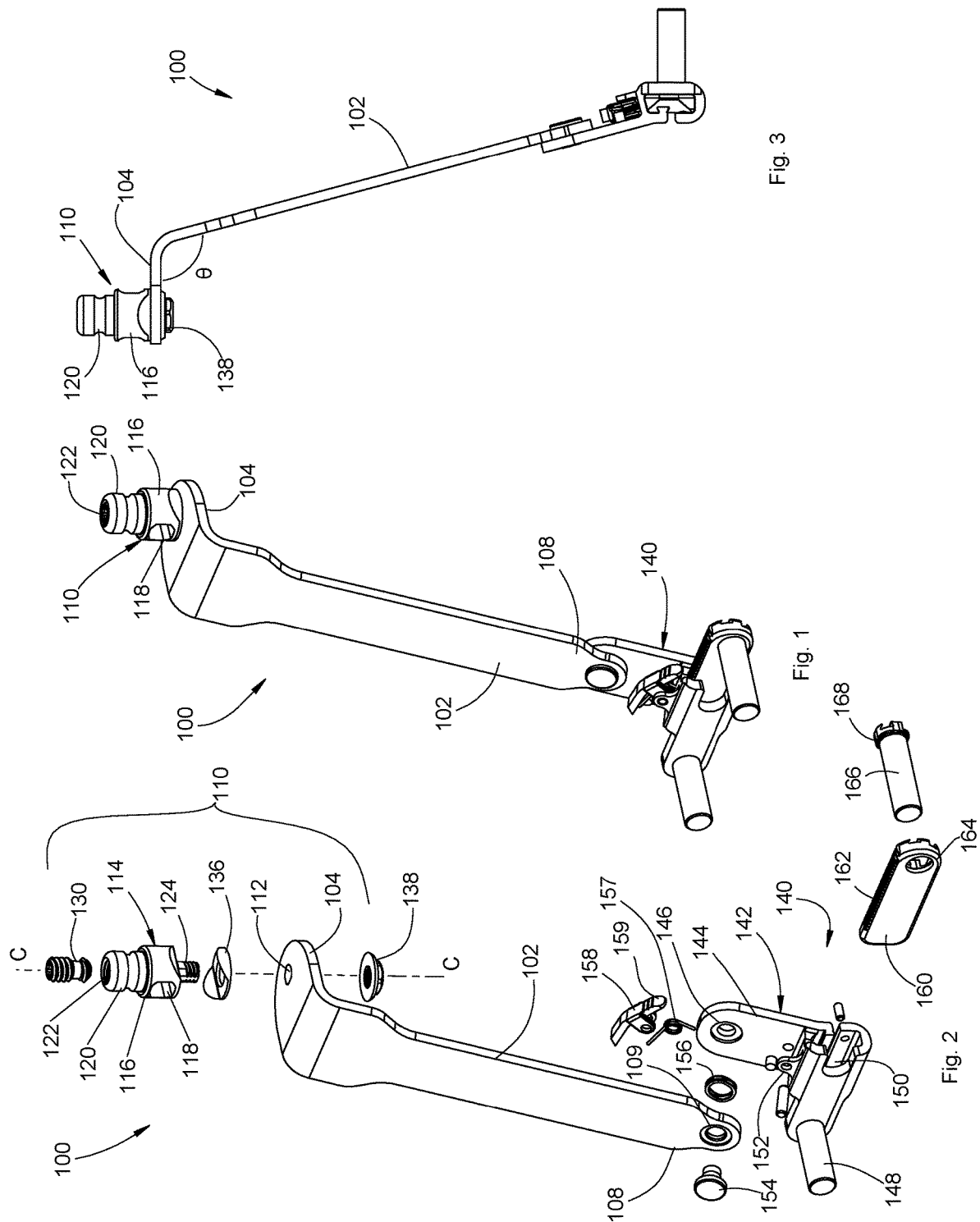

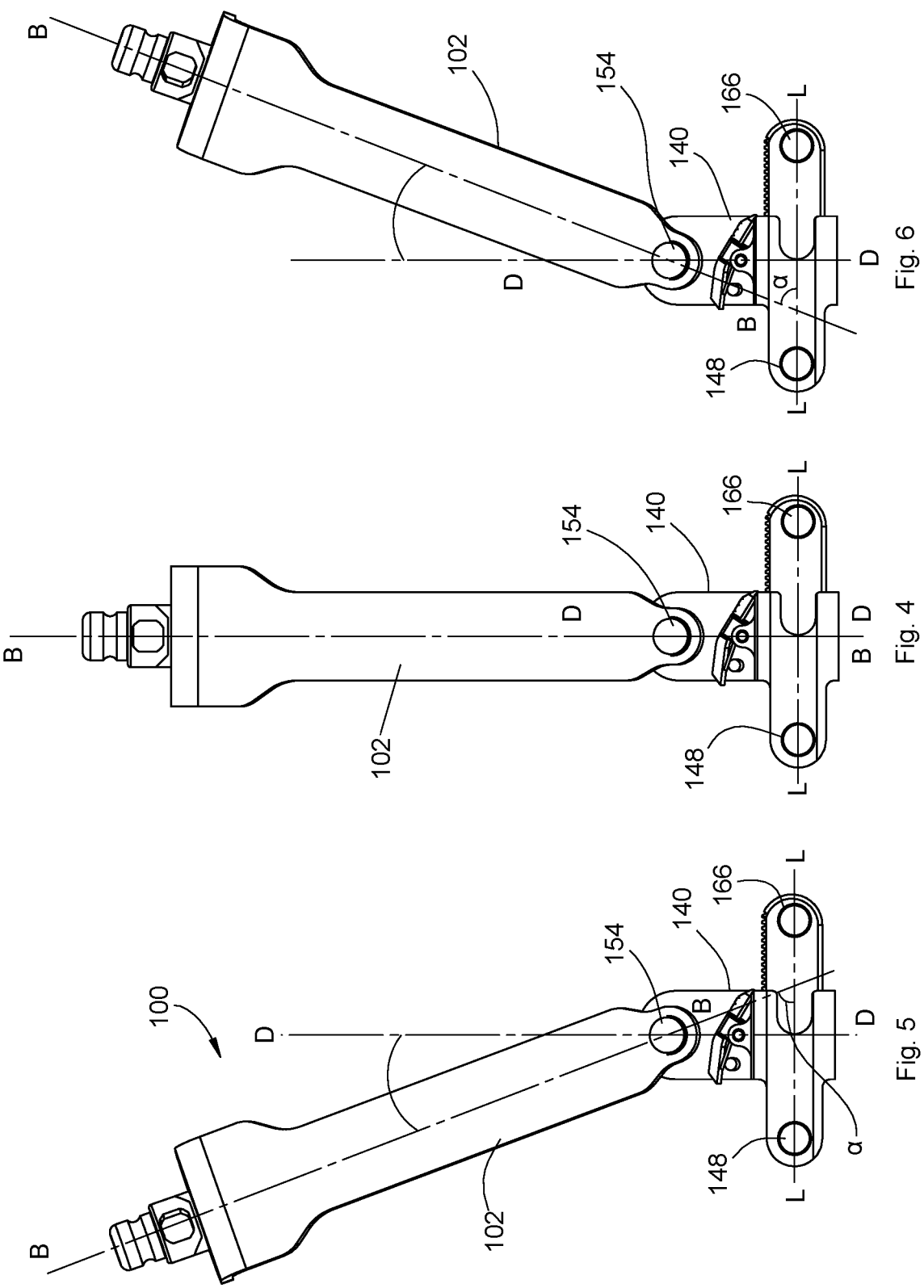

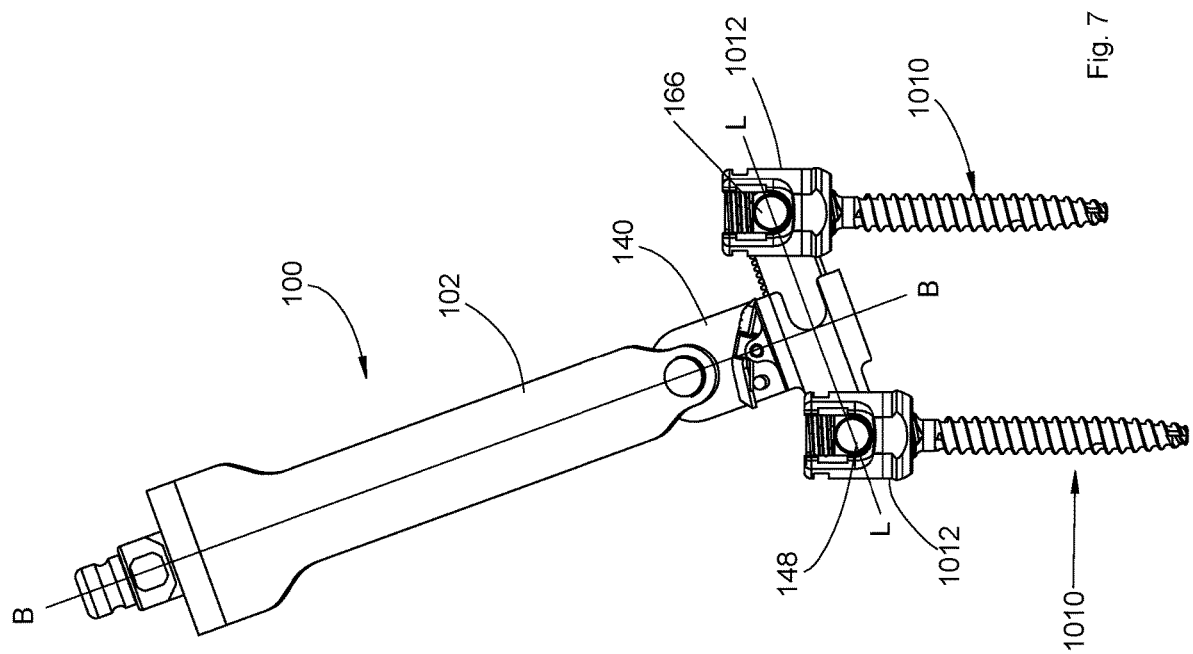

SWIVEL RETRACTOR AND RIGID CONNECTION SYSTEM FOR RETRACTORS

CROSS-REFERENCE TO RELATED APPLICATION

This application claims the benefit of, and priority to, U.S. Provisional Patent Application Ser. No. 62/530,363, filed Jul. 10, 2017, the entire contents of which are hereby incorporated by reference.

BACKGROUND

1. Technical Field

The present disclosure relates to orthopedic spine surgery, and in particular, to devices, systems, and methods for minimally open access retraction devices and surgical methods.

2. Discussion of Related Art

There has been considerable development of retractors and retractor systems for less invasive spine surgery procedures. Previous devices are large and bulky; and not well suited to the smaller incisions and muscle sparing approaches desired for less invasive surgery.

Most retractor systems may be classified as table mounted systems, handheld systems, or soft tissue anchored systems. Table-mounted systems generally contain a retractor attached to a surgical table through a support arm. Generally, table-mounted systems are bulky and provide a clinician with a limited degree of maneuverability. Handheld surgical retractors are well known and can be modified to fit the contours of smaller incisions but require manual manipulation to maintain position during surgery. Soft tissue anchored systems are positioned into the soft tissue and levered back to hold the wound open, frequently requiring re-positioning during a procedure when dislodged or when a view is obstructed by the system. The table mounted systems, handheld systems, and soft tissue anchored systems are all susceptible to displacement in numerous directions as a result of pressure exerted on the patient's body caused by, among other things, the surgeon's work within the body or the patient's breathing. The pressure exerted on the patient's body causes a reactionary force on the retractor and may displace the retractor from its original location.

Accordingly, there is a continuing need for improved retractors that are self-retaining in the incision, are fixed to inhibit dislodgement, do not require re-positioning while allowing manual manipulation to increase a clinician's procedural flexibility, and are minimally obtrusive so as not to interfere with the surgical procedure.

SUMMARY

In an aspect of the present disclosure, a swivel distractor includes a blade portion, a flange, and a distraction portion. The flange extends at an angle from a first end of the blade portion. The distraction portion is pivotally coupled to a second end of the blade portion opposite the first end.

In aspects, the swivel distractor includes a connector that is secured to the flange. The connector may have a body and a nipple that extends proximally form the body. The nipple may be configured to be received within an arm of a support frame to couple the swivel distractor to the arm. The body may define a receiver that is configured to receive a tip of a handle such that the handle forms a rigid construct with the swivel distractor.

In some aspects, the angle that the flange extends from the first end of the blade portion is in a range of about 70° to about 110°. The flange may extend perpendicularly from the first end of the blade portion.

In certain aspects, the distraction portion includes a first foot that is configured to be received in a head of a first pedicle screw and a second foot that is configured to be received in a head of a second pedicle screw. The second foot may be movable relative to the first foot.

In another aspect of the present disclosure, a retractor blade includes a blade portion, a flange, and a connector. The flange extends at an angle from a first end of the blade portion. The connector is secured to the flange and has a body and a nipple that extends proximally from the body. The nipple is configured to be received within an arm of a support frame to couple the retractor blade to the arm. The body defines a receiver that is configured to receive a tip of a handle such that the handle forms a rigid construct with the retractor blade.

In another aspect of the present disclosure, a retractor system includes a support frame, a handle, and a retractor blade. The support frame has a first arm and a second arm. The handle has a tip. The retractor blade includes a blade portion, a blade flange, and a connector. The blade flange extends at an angle from a first end of the blade portion. The connector is secured to the flange and has a body and a nipple that extends proximally from the body. The nipple is releasably received within the first arm of the support frame. The body defines a receiver that receives the tip of the handle such that the handle and the retractor blade form a rigid construct.

In aspects the retraction system includes a swivel distractor having a distractor blade portion, a distractor flange and a distraction portion. The distractor flange extends at an angle from a first end of the distractor blade portion. The distraction portion is pivotally coupled to a second end of the distraction blade portion that is opposite the first end.

In some aspects, the retraction includes a distractor connector that is secured to the distractor flange. The distractor connector may have a body and a nipple that extends proximally from the body. The nipple may be releasably received within the second arm of the support frame.

In certain aspects, the retraction system includes a distractor handle that has a tip. The body of the connector of the distractor may define a receiver that receives the tip of the distractor handle such that the distractor handle and the swivel distractor form a rigid construct.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 1 is a perspective view of a swivel retraction distractor provided in accordance with the present disclosure;

FIG. 2 is an perspective view, with parts separated of the swivel retraction distractor of FIG. 1;

FIG. 3 is a side view of the swivel retraction distractor of FIG. 1;

FIG. 4 is a front view of the swivel retraction distractor of FIG. 1 in an aligned position;

FIG. 5 is a front view of the swivel retraction distractor of FIG. 4 in a first pivoted position;

FIG. 6 is a front view of the swivel retraction distractor of FIG. 4 in a second pivoted position;

FIG. 7 is a front view of the swivel retraction distractor of FIG. 1 in the aligned position and secured to two pedicle screws vertically offset from one another;

DETAILED DESCRIPTION

Figure 8:
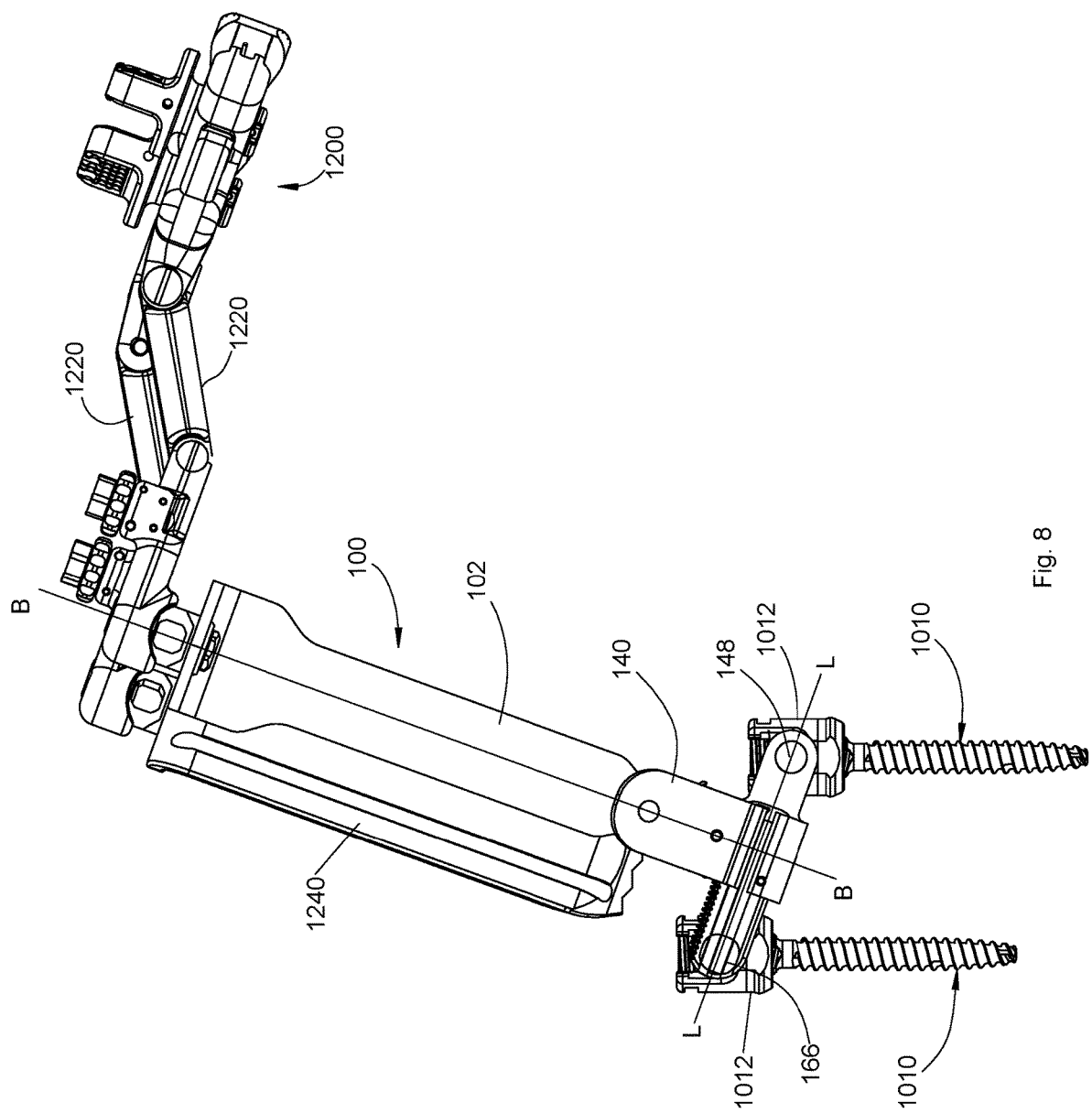
FIG. 8 is a side view of a retraction system having a support frame secured to a retraction blade and the swivel retraction distractor and pedicle screws of FIG. 7.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. Additionally, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring initially to FIGS. 1 and 2, a swivel retractor distractor 100 is provided in accordance with the present disclosure. The swivel retractor distractor 100 includes a retractor blade portion 102 and a proximal flange 104 extending from a proximal end of the retractor blade portion 102. The proximal flange 104 may extend substantially perpendicular to the retractor blade portion 102 and define an angle θ (FIG. 3) in a range of about 70° to about 110° with the retractor blade portion 102.

The proximal flange 104 defines a connector opening 112 therethrough that receives a connector assembly 110. The connector assembly 110 is configured to releasably couple to a manipulation handle 300 (FIG. 15) and/or a support frame 1200 (FIG. 9) as described in detail below. The connector assembly 110 includes a connector 114, a set screw 130, a connector washer 136, and a connector nut 138. The connector 114 has a body 116 that defines a handle receiver 118 that extends through the body 116 and is orthogonal to a longitudinal axis C-C of the connector 114. The connector 114 also includes a nipple 120 that extends proximally from the body 116. The nipple 120 defines a threaded screw opening 122 that extends along the axis C-C and is in communication with the handle receiver 118. As detailed below, the set screw 130 is threadably received within the screw opening 122 and may interfere with, or extend into, the handle receiver 118. Further, the connector 114 includes a connector shaft 124 that extends distally from the body 116. The connector shaft 124 extends along the axis C-C and passes through the connector washer 136, the connector opening 112, and the connector nut 138. The connector nut 138 secures the connector 114 to the proximal flange 104 of the swivel retractor blade 100.

The swivel retractor distractor 100 includes a distractor portion 140 pivotally coupled to a distal portion 108 of the retractor blade portion 102. The distractor portion 140 includes a swivel body 142 having a swivel flange 144 and a fixed foot 148. The swivel flange 144 is defined in a plane substantially parallel to a plane defined by the retractor blade portion 102. The swivel flange 144 defines an opening 146 that receives a swivel connector 154 that passes through an opening 109 defined in the distal portion 108 of the retractor blade portion 102 to pivotally couple the distractor portion 140 to the retractor blade portion 102. The distractor portion 140 may include a swivel washer 156 disposed about the swivel connector 154 to secure the swivel connector 154 within the opening 109 and the opening 146 of the swivel flange 144. The swivel washer 156 may provide resistance to pivoting of the distractor portion 140 relative to the retractor blade portion 102 such that a force is required to pivot the distractor portion 140 relative to the retractor blade portion 102. The swivel washer 156 may be a wave spring washer. It is contemplated that the distractor portion 140 may be selectively locked in place relative to the retractor blade portion 102.

The fixed foot 148 of the distractor portion 140 extends orthogonally away from the swivel flange 144 and is configured to be received in a head 1012 of a pedicle screw 1010 (FIG. 7). The distractor portion 140 also includes a distracting or movable foot 166 that is movably coupled to the swivel body 142. The movable foot 166 is secured to a leg 160. The leg 160 includes a row of teeth 162 along a top or proximal edge and defines an opening 164. The movable foot 166 is received within the opening 164 and includes a flange 168 that prevents the movable foot 166 from passing entirely through the opening 164.

The swivel body 142 defines a channel 150 that slidably receives the leg 160 therein. The swivel body 142 also includes a lock 158 having a finger 159 that is pivotally secured to a lock mount 152 of the swivel body 142. A biasing member 157, e.g., a torsion spring, biases the lock 158 such that the finger 159 sequentially engages the teeth 162 of the leg 160 to lock the leg 160 relative to the swivel body 142 such that a distance between the fixed foot 148 and the movable foot 166 is fixed. A distraction portion having a similar fixed foot and movable foot is disclosed in U.S. Pat. No. 8,979,749 (hereinafter "the '749 patent") which is hereby incorporated by reference in its entirety.

With reference to FIGS. 4-6, the distraction portion 140 is pivotal relative to the retractor blade portion 102 between an aligned position (FIG. 4), a first pivoted position (FIG. 5), and a second pivoted position (FIG. 6). Specifically, the retractor blade portion 102 defines a blade axis B-B, the distraction portion 140 defines an axis D-D, and a leg axis L-L passes through center points of the fixed foot 148 and the movable foot 166. As shown, the leg axis L-L is orthogonal to the axis D-D of the distraction portion 140; however, it is contemplated that the leg axis L-L may be disposed at a nonorthogonal angle, e.g., transverse angle, relative to the axis D-D.

In the aligned position, the distraction portion 140 is pivoted relative to the retraction blade portion 102 such that the leg axis L-L is orthogonal to the blade axis B-B as shown in FIG. 4. In the aligned position, the axis D-D of the distraction portion 140 may be parallel to the blade axis B-B. In the first pivoted position, the distraction portion 140 is pivoted about the swivel connector 154 in a first direction such that the leg axis L-L defines an angle α with respect to the blade axis B-B, which is less than 90°. For example, the angle α may be in a range of about 30° to about 90°. In the second pivoted position, the distraction portion 140 is pivoted about the swivel connector 154 in a second direction, opposite the first direction, such that the leg axis L-L defines an angle α with respect to the blade axis B-B, which is less than 90°.

With reference to FIGS. 7-12, the swivel retractor distractor 100 is used to compensate for height variations between two pedicle screws 1010 that may be vertically offset from one another. It will be appreciated that traditional retractor distractors, like those disclosed in the '749 patent, are fixed in a configuration similar to the aligned position of the swivel retractor distractor 100 of FIGS. 7-9. In such a configuration, when the feet 148, 166 of the distractor portion 140 are secured in heads 1012 of pedicle screws 1010 that are offset from one another, e.g., vertically offset, the offset of the heads 1012 of the pedicle screws 1010 is transferred to ancillary structures secured to the swivel retractor distractor 100. For example, when the swivel retractor distractor 100 is releasably secured to an arm 1220 of a support frame 1200, the offset of the heads 1012 of the pedicle screws 1010 is transferred to the support frame 1200. When the support frame 1200 is also used to support a retractor blade 1240 with another arm 1220, the offset is also transferred to the retractor blade 1240.

Figure 9:
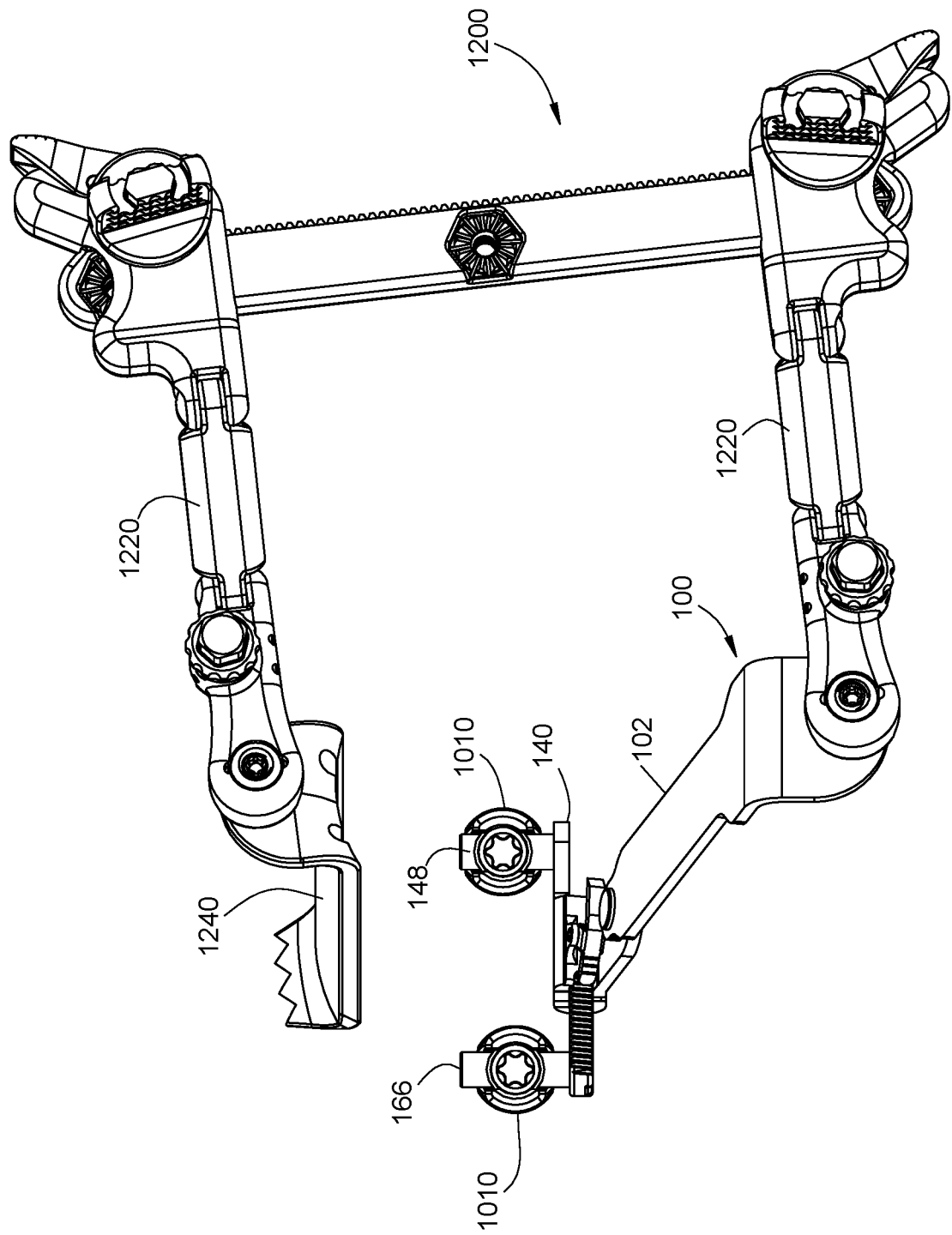
FIG. 9 is a top view of the retraction system of FIG. 8.

With particular reference to FIG. 9, by transferring the offset to the retractor blade 1240, the angle of the retractor blade 1240 to a surgical site may be suboptimal, which may compromise a clinician's vision or access to a portion of a surgical site. For example, as shown in FIG. 9, when viewed from directly above the pedicle screws 1010, the retractor blade 1240 may block a portion of the surgical site.

Figure 10:
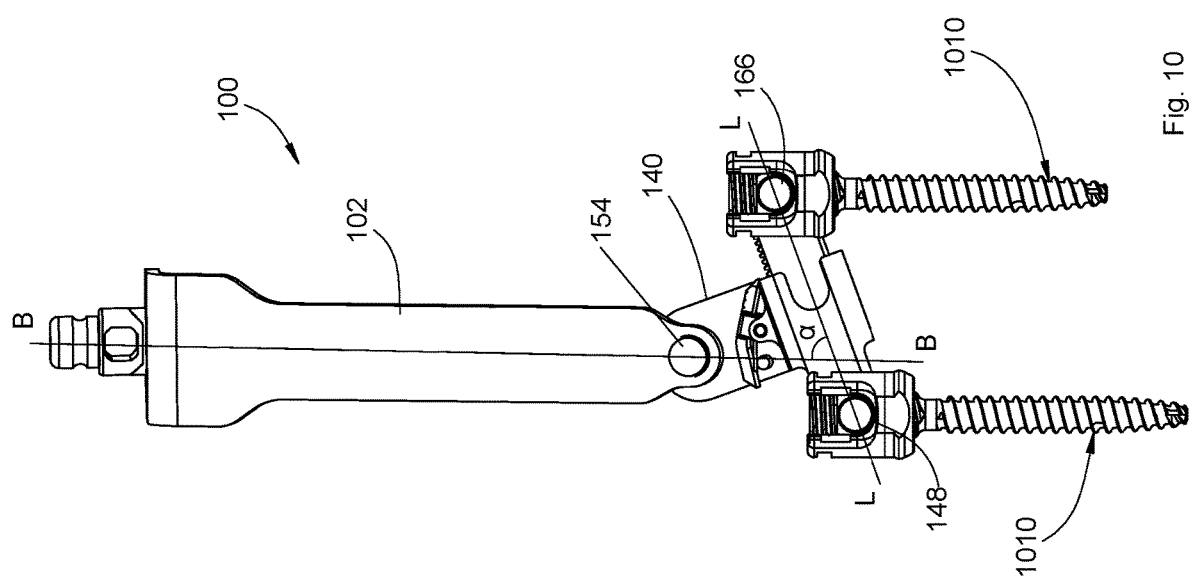
FIG. 10 is a front view of swivel retraction distractor of FIG. 1 in the second pivoted position and secured to two pedicle screws vertically offset from one another.
Figure 11:
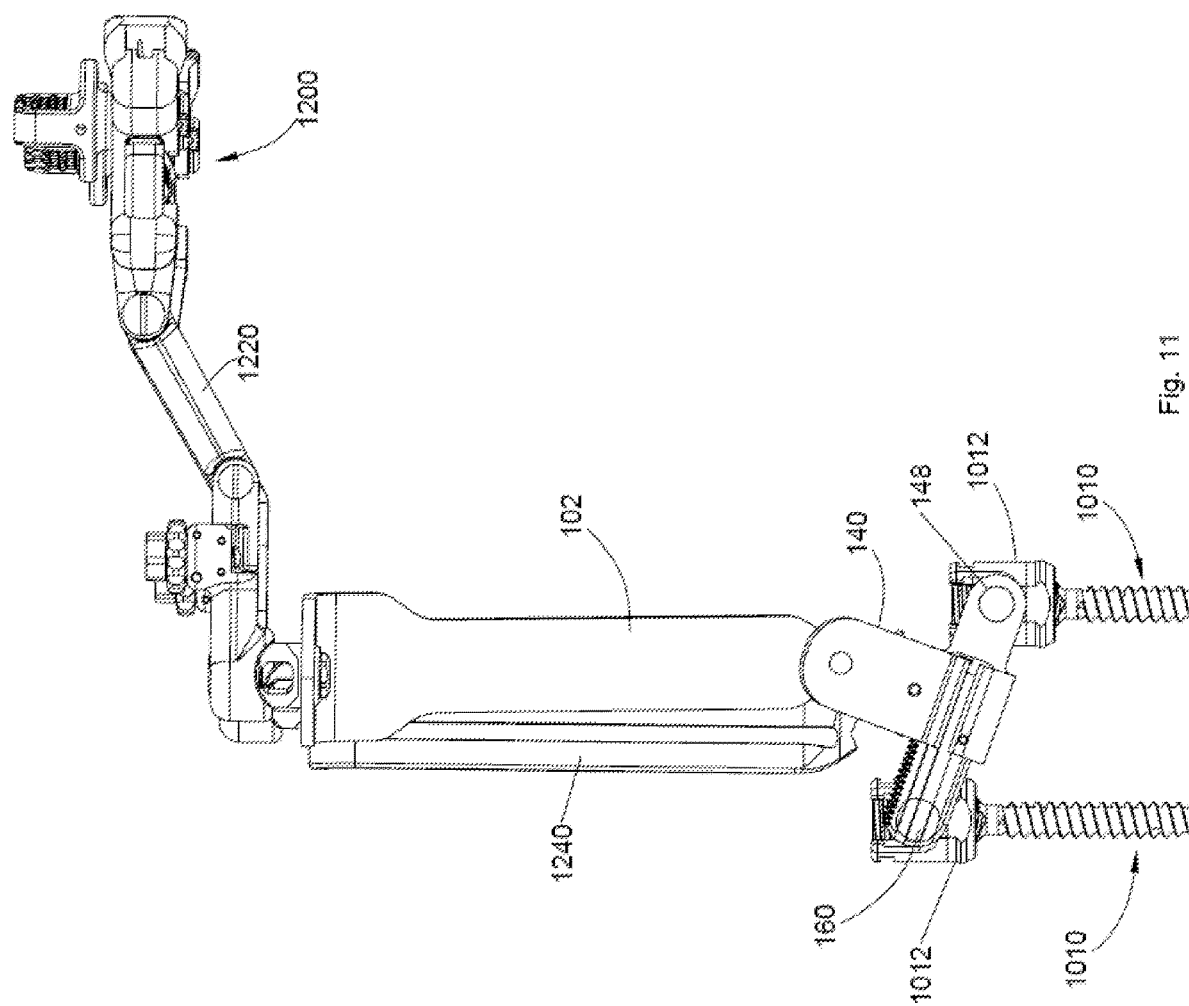
FIG. 11 is a side view of the retraction system of FIG. 8 with the swivel retraction distractor shown in the second pivoted position.
Figure 12:
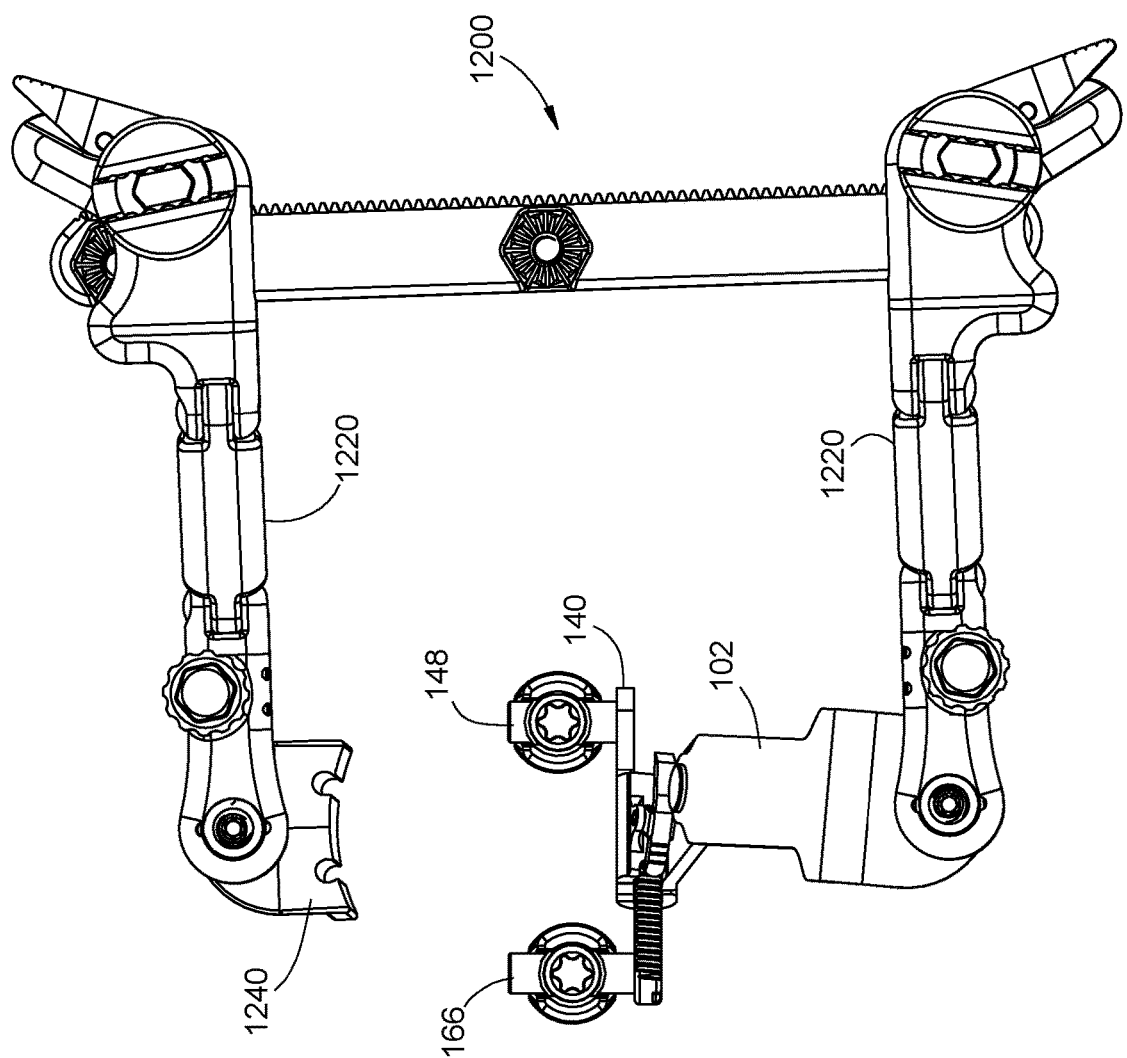
FIG. 12 is a top view of the retraction system of FIG. 11.

With particular reference to FIGS. 10-12, the first and second articulated configurations of the swivel retractor distractor 100 allow the swivel retractor distractor 100 to compensate for the offset between the pedicle screws 1010 such that the offset is not transferred to ancillary structures secured to the swivel retractor distractor 100. Specifically, as shown in FIG. 10, the retractor blade portion 102 of the swivel retractor distractor 100 is pivoted about the swivel connector 154 such that the blade axis B-B is substantially parallel with longitudinal axes of the pedicle screws 1010. As shown in FIG. 11, when the swivel retractor distractor 100 is secured to the arm 1220 of the support frame 1200, the retractor blade 1240 secured to another arm 1220 is also aligned with the longitudinal axes of the pedicle screws 1010. In this instance, when viewed from directly above the pedicle screws 1010, the retractor blade 1240 is vertically aligned with the pedicle screws such that the view of the surgical site is optimal as shown in FIG. 12.

Figure 13:
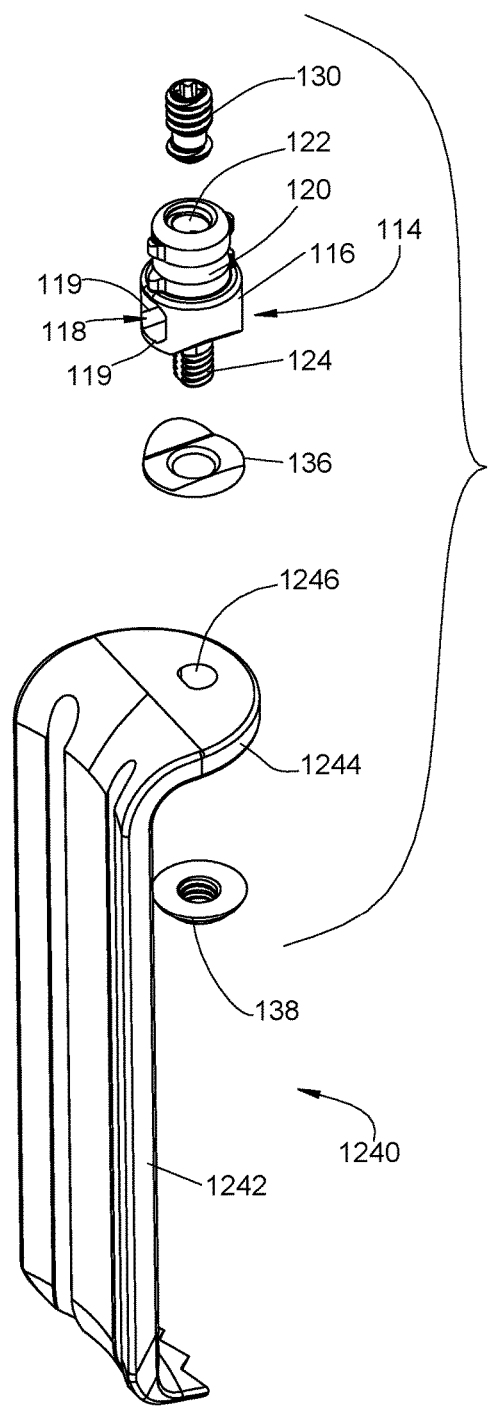
FIG. 13 is an perspective view, with parts separated, of a retractor blade provided in accordance with the present disclosure.

Referring now to FIG. 13, the connector assembly 110 is described in accordance with the present disclosure and the retractor blade 1240. It will be appreciated that the connector assembly 110 can also be used with the swivel retractor distractor 100 of FIG. 1. The retractor blade 1240 has a blade portion 1242 and a proximal flange 1244 that extends substantially perpendicular to a proximal portion of the blade portion 1242. The proximal flange 1244 defines an opening 1246 that is configured to receive the connector shaft 124 of the connector 114 to secure the connector assembly 110 to the proximal flange 1244. Specifically, the connector shaft 124 is threaded into the connector nut 138, which may be welded to the connector shaft 124 and/or the proximal flange 1244, to fix the connector 114 to the proximal flange 1244. In addition, the connector shaft 124 and the opening 1246 of the proximal flange 1244 may be complementary D-shaped such that a flat 125 (FIG. 16) of the connector shaft 124 may prevent the connector shaft 124 from rotating relative to the proximal flange 1246 when the connector shaft 124 is received within the opening 1246.

The connector washer 136 is disposed between the connector 114 and the proximal flange 1244 with the connector shaft 124 passing through the connector washer 136. The connector washer 136 may rotatably fix or assist in rotatably fixing the connector 114 relative to the proximal flange 1244. The connector washer 136 may be colored to indicate a property of the retractor blade 1240. For example, the connector washer 136 may be blue to indicate that the retractor blade 1240 has a first length and may be green to indicate that the retractor blade 1240 has a second length that is different from the first length. Additionally or alternatively, the connector washer 136 may be red to indicate that the proximal flange 1244 is perpendicular to the blade portion 1242 and may be white to indicate that the proximal flange 1244 is disposed at an 85° angle relative to the blade portion 1242. It is contemplated that the connector washer 136 may have a color and/or a pattern to indicate one or more properties of the retractor blade 1240. By providing a connector washer 136 with visual indicators of one or more properties of the retractor blade 1240, a clinician can quickly identify a desired retractor blade 1240 during a surgical procedure.

Figure 14:
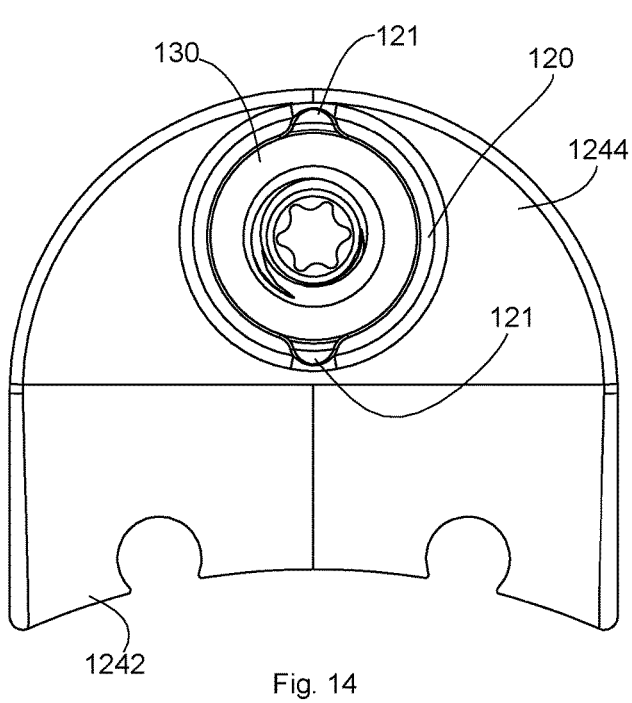
FIG. 14 is a top view, with parts assembled, of the retractor blade of FIG. 13.
Figure 15:
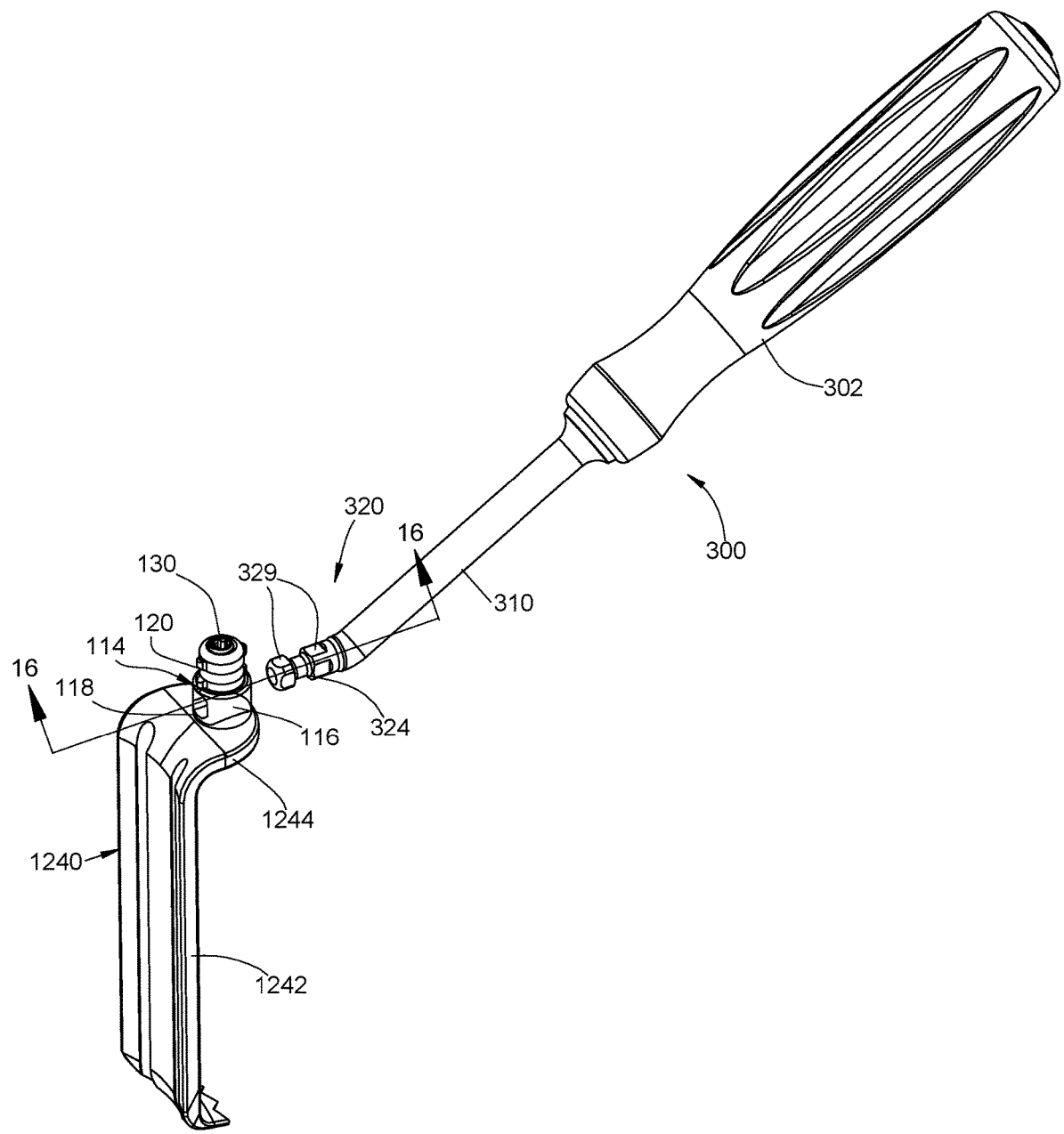
FIG. 15 is a perspective view of the retractor blade of FIG. 13 and a manipulation handle having a tip.

Referring briefly to FIGS. 14 and 15, the nipple 120 of the connector 114 includes tabs 121 to prevent the connector 114, and thus the retractor blade 1240, from rotating relative to an arm 1220 (FIG. 12) when the retractor blade 1240 is secured to the arm 1220. In addition, the nipple 120 defines a groove 123 about an outer surface of the nipple 120 that is configured to receive a retaining member, e.g., a ball detent, of the arm 1220 to releasably secure the connector 114 to the arm 1220.

Figure 16:
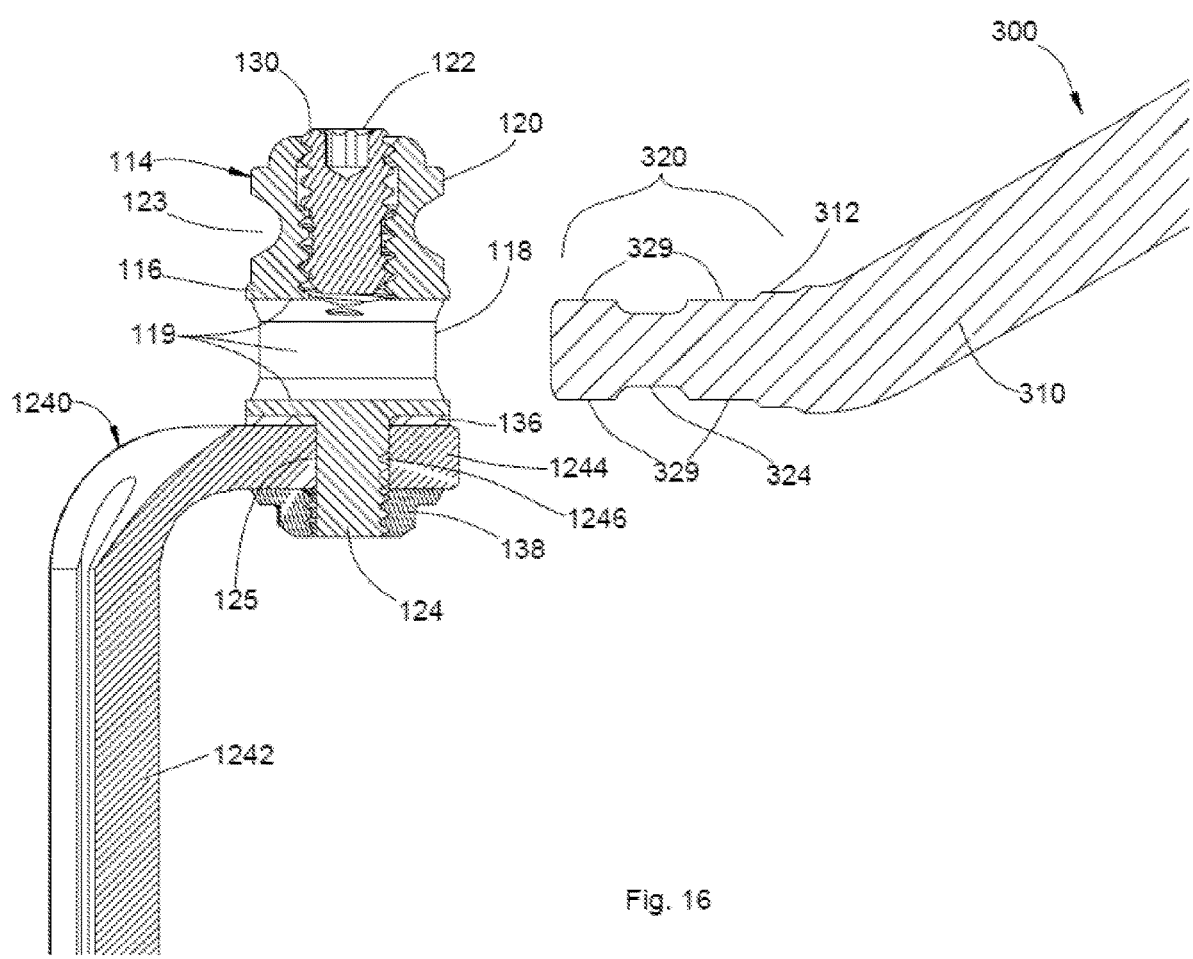
FIG. 16 is an enlarged, cross-sectional view taken along section line 16-16 of FIG. 15.
Figure 17:
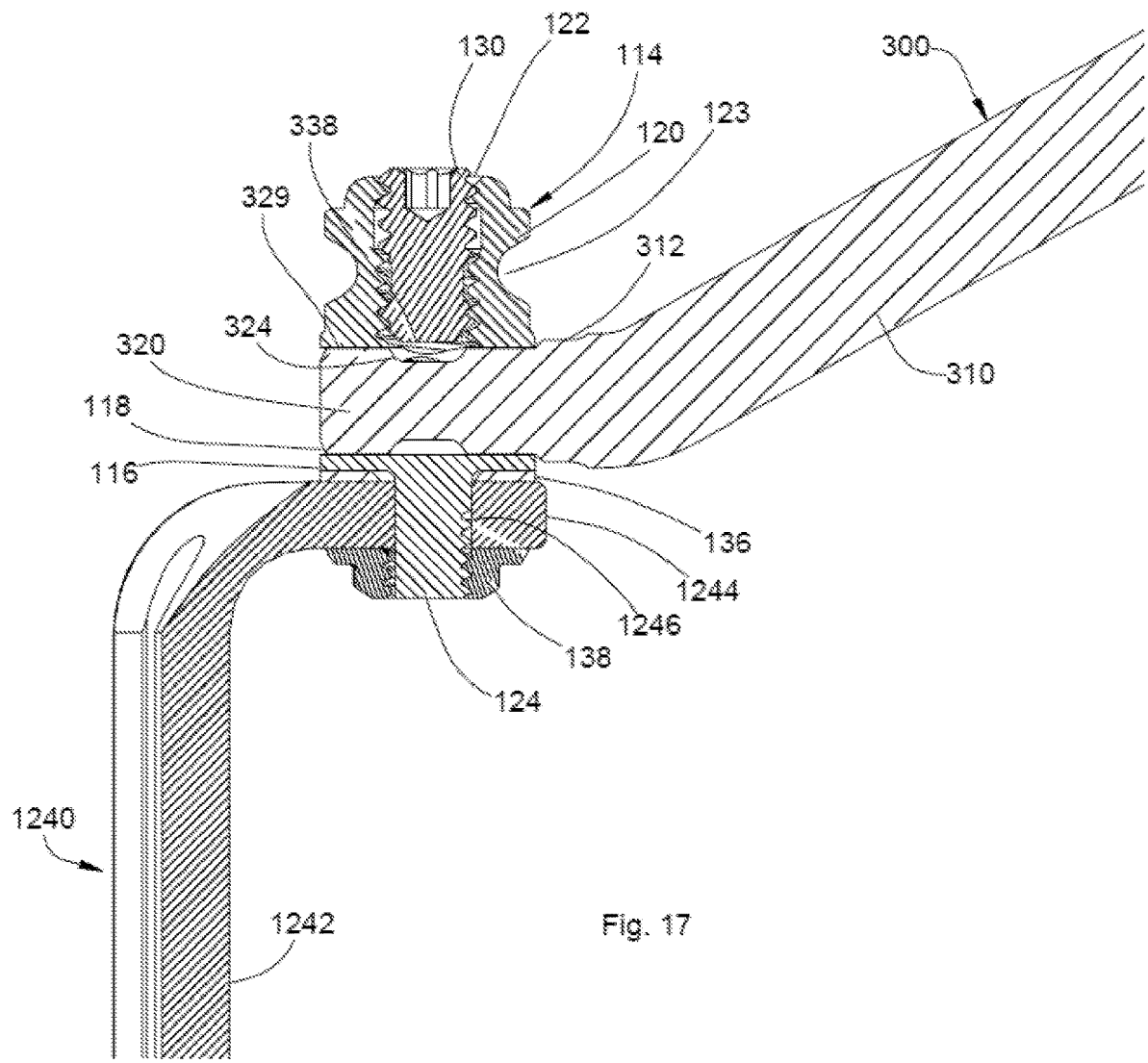
FIG. 17 is another view of FIG. 16 with the tip of the manipulation handle received within a connector of the retractor blade.
Figure 18:
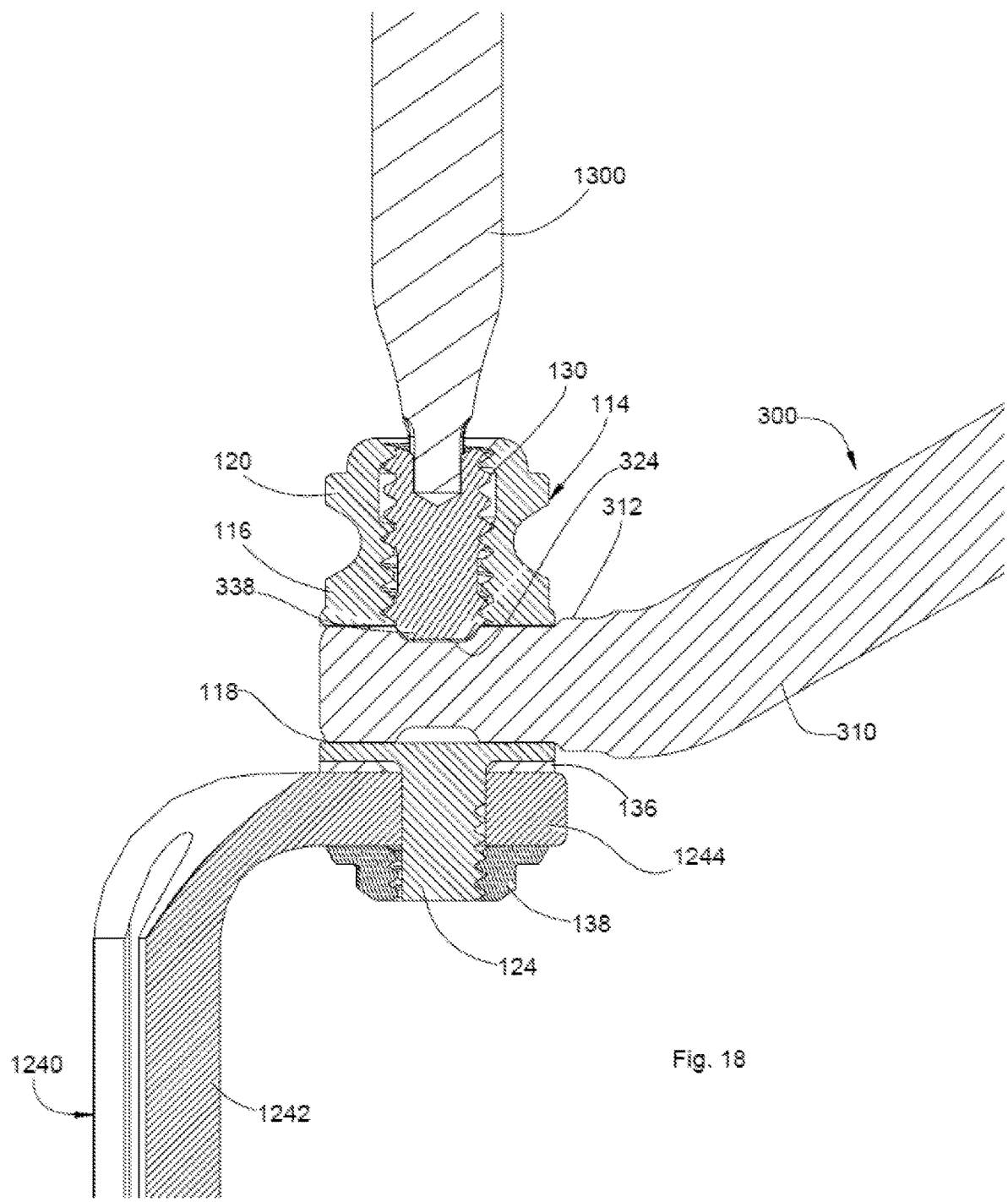
FIG. 18 is another view of FIG. 17 with a screwdriver engaged with a set screw to secure the tip within the connector to form a rigid construct.

With reference to FIGS. 15 and 16, a manipulation handle 300 includes a handle 302, an elongate shaft 310 extending from the handle 302, and a tip 320 extending from the elongate shaft 310. The tip 320 may be disposed at an angle relative to the elongate shaft 310. The connector 114 is configured to receive the tip 320 of the manipulation handle 300 such that the manipulation handle 300 can be used to manipulate the retractor blade 1240 as described in detail below. Specifically, the body 116 of the connector 114 defines the handle receiver 118 that is configured to receive the tip 320. The walls defining the handle receiver 118 have flats 119 that complement flats 329 of the tip 320 to rotatably fix the manipulation handle 300 to the retractor blade 1240 when the tip 320 is received within the handle receiver 118. The tip 320 also defines a slot 324 longitudinally disposed between the flats 329 that is configured to receive a portion of the set screw 130 to prevent the tip 320 from withdrawing from the handle receiver 118 as shown in FIG. 17. Specifically, when the tip 320 is fully disposed within the handle receiver 118, the set screw 330 is tightened such that a distal end 338 of the set screw 330 is disposed within the slot 324 of the tip 320. The slot 324 may have flats aligned with the flats 329 such the distal end 338 of the set screw 330 engages the flat of the slot 324 to further prevent the tip 320 from rotating within the connector 114. A screwdriver 1300 may be used to tighten the set screw 130. The set screw 330 may mate with the tip 320 such that the manipulation handle 300 and the retraction blade 1240 form a rigid construct with one another as shown in FIG. 18. In addition, the elongate shaft 310 may have a distal boss 312 that abuts the body 116 of the connector 114 when the tip 320 is properly positioned or fully disposed within the handle receiver 118 of the connector 114.

Figures 19A, 19B:
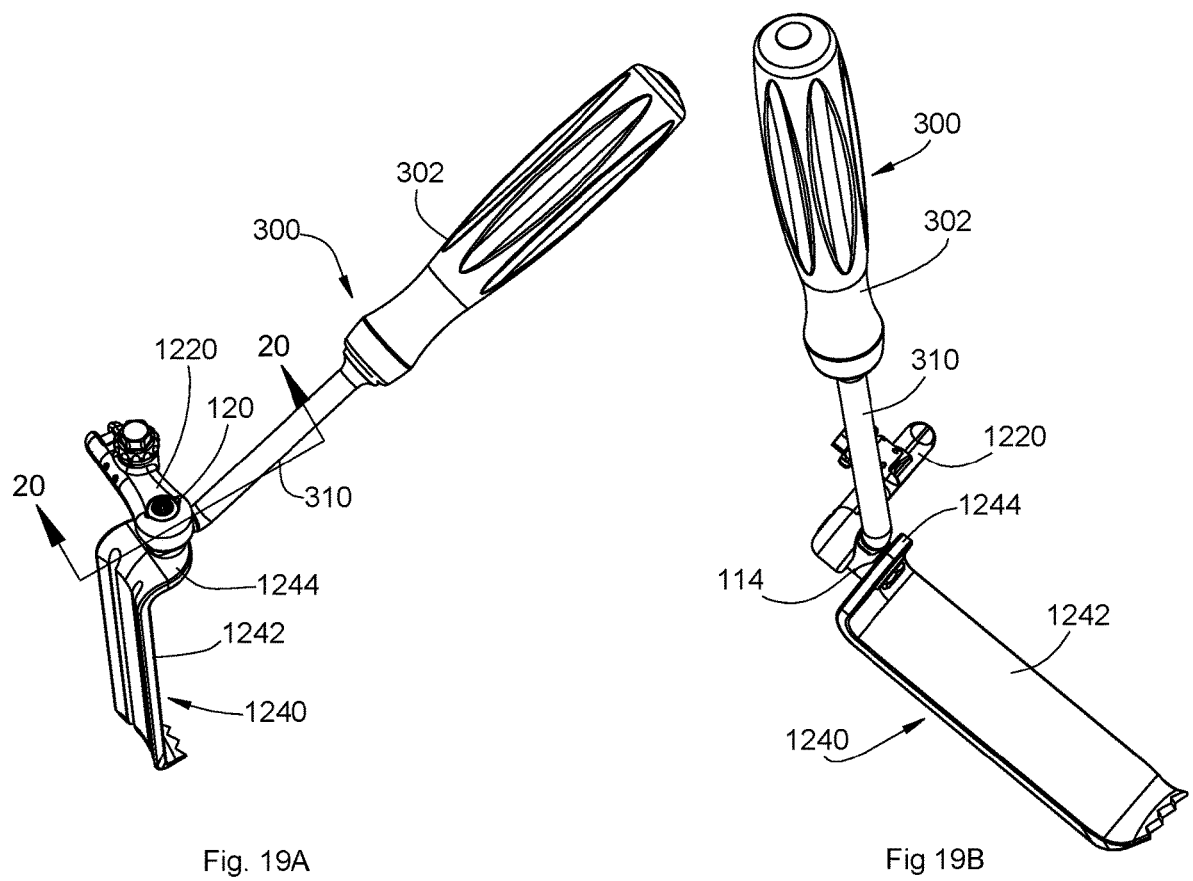
FIGS. 19A and 19B are perspective views of the rigid construct of the manipulation handle and the retractor blade.
Figure 20:
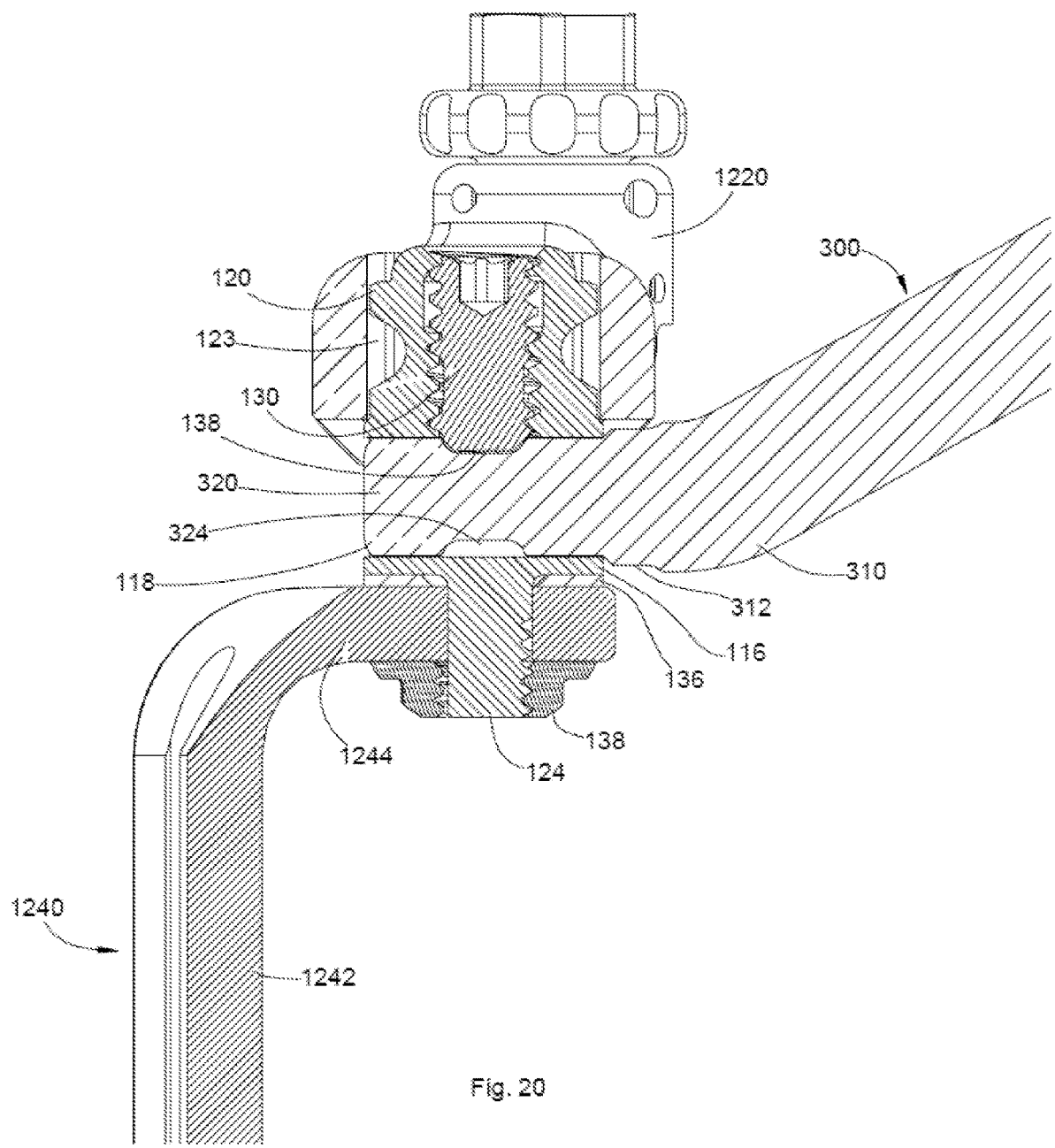
FIG. 20 is an enlarged, cross-sectional view taken along section line 20-20 of FIG. 19A.

Referring now to FIGS. 19A, 19B, and 20, the nipple 120 of the connector 114 can be secured within the arm 1220 when tip 320 of the manipulation handle 300 is also received within the handle receiver 118 of the connector 114 such that the manipulation handle 300 can be used to manipulate the retractor blade 1240 when the retractor blade 1240 is secured to the frame 1200 (FIG. 12). It is contemplated that the retractor blade 1240 may be semi-constrained by the arm 1220 and that the manipulation handle 300 may be used to manipulate the retractor blade 1240, e.g., toe the retractor blade 1240, and then the arm 1220, in cooperation with the frame 1200, can be tightened to fully constrain the retractor blade 1240. Once the retractor blade 1240 is fully constrained, the set screw 130 can be loosened and the manipulation handle 300 removed from within the handle receiver 118.

Figure 21:
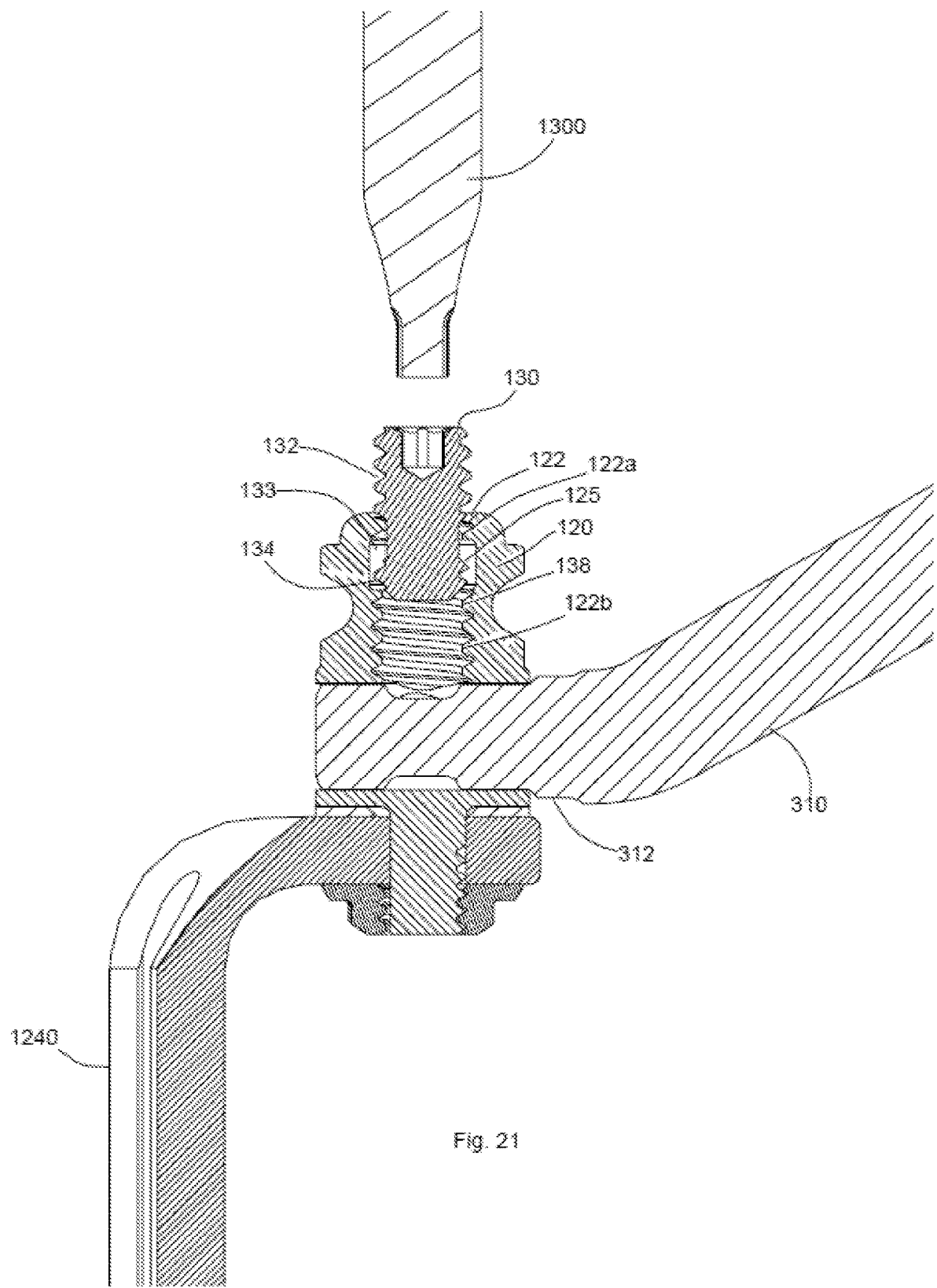
FIG. 21 is another view of FIG. 18 with the set screw shown backed out and the screwdriver separated therefrom.

Referring to FIG. 21, the set screw 130 and the nipple 120 can include a retention system to prevent the set screw 130 from inadvertently separating or falling out of the nipple 120 during a surgical procedure. Specifically, the threaded opening 122 of the nipple 120 may include a proximal threaded section 122a, a distal threaded section 122b, and an unthreaded section 125 disposed between the proximal and distal threaded sections 122a, 122b. In addition, the set screw 130 may include an unthreaded segment 133 disposed between a first or proximal threaded segment 132 and a second or distal threaded segment 134. As the set screw 130 is loosened, the first threaded segment 132 and the second threaded segment 134 disengage the first threaded section 122a and the distal threaded section 122b at the same time such that the second threaded segment 134 is disposed within the unthreaded section 125 and the unthreaded segment 133 is disposed within the proximal threaded section 122. In such a position, the threads of the set screw 130 are fully disengaged from the threads of the nipple 120 such that a proximal or distal force, upward or downward force as shown, is required to reengage the threads and continue to tighten or loosen the set screw 130. It will be appreciated that this configuration prevents the set screw 130 from inadvertently separating form the nipple 120.

Figure 22:
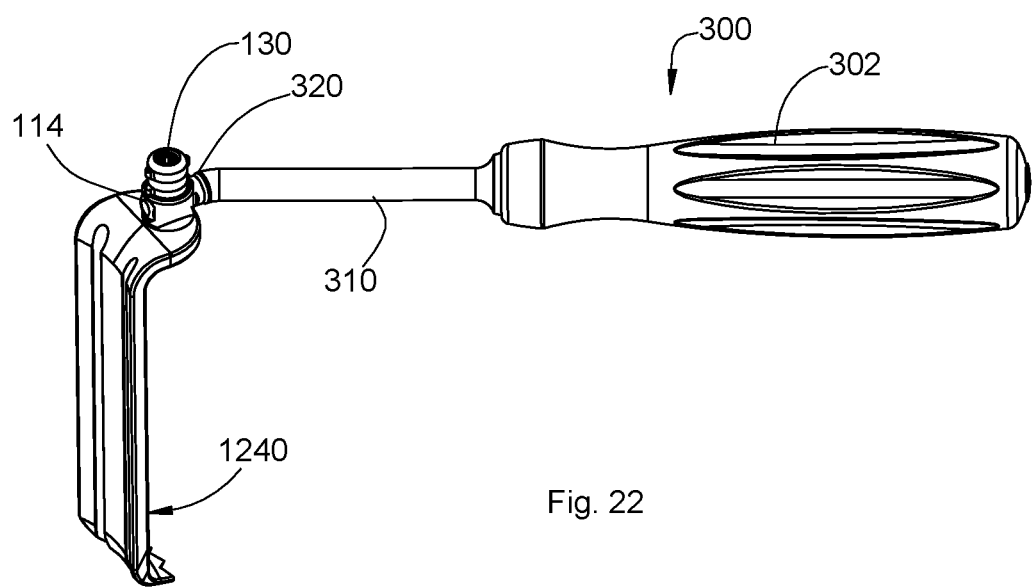
FIG. 22 is a perspective view of the manipulation handle and retractor blade of FIG. 15 shown rigidly secured together with the manipulation handle illustrated in a second position.

With reference to FIGS. 16 and 22, the configuration of the handle receiver 118 of the connector 114 and the tip 320 allow the manipulation handle 300 to form a rigid construct with the retractor blade 1240 in a plurality of positions. Specifically, the number of flats 119 of the handle receiver 118 and the flats 329 of the tip 320 may determine the number of positions that the manipulation handle 300 may be rigidly secured to the retractor blade 1240. As shown, each of the handle receiver 118 and the manipulation handle 300 have four flats 119, 329, respectively, such that the manipulation handle 300 can be rigidly secured in eight positions relative to the retractor blade 1240. For example, as shown in FIG. 22, the manipulation handle 300 is rigidly secured to the retractor blade 1240 and rotated about 90° from the opposite side when compared to the position shown in FIG. 16. It will be appreciated that either the handle receiver 118 or the tip 320 may have number of flats, e.g., a greater or lesser number of flats 119, 329, respectively. In addition, the handle receiver 118 and the tip 320 are not required to have the same number of flats 119, 329 as the other one of the handle receiver 118 and the tip 320 as long as the flats 119, 329 cooperate to prevent rotation of the tip 320 relative to the connector 114.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A swivel distractor comprising: a blade portion with a first central longitudinal axis along a length of the blade portion;
    a flange extending at an angle from a first end of the blade portion; and
    a distraction portion including a first part and a second part abutting the first part, the first part pivotally coupled to a second end of the blade portion opposite the first end, the first part of the distraction portion having a centerline along its length, and the second part having an adjustable length, wherein the distraction portion is pivotable between a first position where the centerline of the first part is on a first side of the first central longitudinal axis and a second position where the centerline of the first part is on a second side of the first central longitudinal axis, the second side being opposite the first side.

2. The swivel distractor according to claim 1, further comprising a connector secured to the flange, the connector having a body and a nipple extending proximally from the body, the nipple configured to be received within an arm of a support frame to couple the swivel distractor to the arm, the body defining a receiver configured to receive a tip of a handle such that the handle forms a rigid construct with the swivel distractor.

3. The swivel distractor according to claim 2, wherein the receiver is defined by a connector flat that extends through the body, the connector flat configured to complement a handle flat of the of the tip of the handle to rotatably fix the handle to the connector.

4. The swivel distractor according to claim 2, wherein the receiver is defined by a plurality of connector flats that extends through the body, each connector flat of the plurality of connector flats configured to complement a handle flat of the of the tip of the handle to rotatably fix the handle to the connector such that the handle is fixable in a plurality of radial orientations relative to the blade portion.

5. The swivel distractor according to claim 2, wherein the connector is configured to fix the tip of the handle in a first orientation and is configured to fix the tip of the handle in a second orientation radially offset from the first orientation.

6. The swivel distractor according to claim 5, wherein the second orientation is radially offset from the first orientation by about 90 degrees.

7. The swivel distractor according to claim 2, wherein the connector includes a screw opening defined through the nipple and in communication with the receiver.

8. The swivel distractor according to claim 7, further comprising a set screw threadably received within the screw opening and configured to engage the tip of the handle to longitudinally fix the handle to the swivel distractor.

9. The swivel distractor according to claim 1, wherein the angle that the flange extends from the first end of the blade portion is in a range of about 70° to about 110°.

10. The swivel distractor according to claim 3, wherein the flange extends perpendicularly from the first end of the blade portion.

11. The swivel distractor according to claim 1, wherein the second part of the distraction portion includes a first foot configured to be received in a head of a first pedicle screw and a second foot, movable relative to the first foot, the second foot configured to be received in a head of a second pedicle screw.

12. The swivel distractor according to claim 11, further comprising a lock configured to selectively fix a position of the second foot relative to a position of the first foot.

13. The swivel distractor according to claim 1, wherein the distraction portion is selectively lockable relative to the blade portion.

14. The swivel distractor according to claim 1, further comprising a swivel connector configured to pass through the blade portion and the distraction portion to pivotally couple the distraction portion to the blade portion.

15. The swivel distractor according to claim 14, further comprising a washer disposed about the swivel connector and configured to resist pivoting of the distraction portion relative to the blade portion.

16. A retraction system comprising:
a support frame having a first arm and a second arm;
a handle having a tip; and
a swivel distractor including:
a blade portion with a first central longitudinal axis along a length of the blade portion;
a blade flange extending at an angle from a first end of the blade portion;
a connector secured to the blade flange, the connector having a body and a nipple extending proximally from the body, the nipple releasably received within the first arm of the support frame, the body defining a receiver that receives the tip of the handle such that the handle and the retractor blade form a rigid construct; and
a distraction portion including a first part and a second part abutting the first part, the first part pivotally coupled to a second end of the blade portion opposite the first end, the first part of the distraction portion having a centerline along its length, and the second part having an adjustable length,
wherein the distraction portion is pivotable between a first position where the centerline of the first part is on a first side of the first central longitudinal axis and a second position where the centerline of the first part is on a second side of the first central longitudinal axis, the second side being opposite the first side.

17. The retraction system according to claim 16, wherein the first part of the distraction portion includes;
a distractor flange extending at an angle from a first end of the distractor portion.

18. The retraction system according to claim 16, wherein the second part of the distraction portion includes a first foot configured to be received in a head of a first pedicle screw and a second foot, movable relative to the first foot, the second foot configured to be received in a head of a second pedicle screw.

19. A swivel distractor comprising:
a blade portion;
a flange extending at an angle from a first end of the blade portion;
a connector secured to the flange, the connector having a body and a nipple extending proximally from the body, the nipple configured to be received within an arm of a support frame to couple the swivel distractor to the arm, the body defining a receiver configured to receive a tip of a handle such that the handle forms a rigid construct with the swivel distractor, and the nipple defining a screw opening, the screw opening being in communication with the receiver; and
a distraction portion pivotally coupled to a second end of the blade portion opposite the first end.

20. The swivel distractor according to claim 19, further comprising a set screw threadably received within the screw opening and configured to engage the tip of the handle to longitudinally fix the handle to the swivel distractor.

* * * * *